(12) United States Patent
Probst et al.

(10) Patent No.: US 8,124,354 B2
(45) Date of Patent: Feb. 28, 2012

(54) METHOD AND IMMUNOABSORBENTS FOR SPECIFIC DETECTION AND ABSORPTION OF ANTIBODIES ASSOCIATED WITH CELIAC DISEASE AND DERMATITIS HERPETIFORMIS

(75) Inventors: Christian Probst, Ratzeburg (DE); Wolfgang Schlumberger, Gross Grönau (DE); Winfried Stöcker, Gross Gröcker (DE); Cornelia Dähnrich, Gross Grönau (DE); Lars Komorowski, Ratzeburg (DE); Thomas Mothes, Leipzig (DE)

(73) Assignee: Euroimmun Medizinische Labordiagnostika AG, Lubeck (DE)

( * ) Notice: Subject to any disclaimer, the term of this patent is extended or adjusted under 35 U.S.C. 154(b) by 177 days.

(21) Appl. No.: 12/602,321

(22) PCT Filed: Apr. 25, 2008

(86) PCT No.: PCT/DE2008/000713
§ 371 (c)(1),
(2), (4) Date: Nov. 30, 2009

(87) PCT Pub. No.: WO2008/145084
PCT Pub. Date: Dec. 4, 2008

(65) Prior Publication Data
US 2010/0203558 A1      Aug. 12, 2010

(30) Foreign Application Priority Data
May 30, 2007   (DE) .......................... 10 2007 025 291

(51) Int. Cl.
*G01N 33/53*   (2006.01)
(52) U.S. Cl. ........................... 435/7.1; 435/86; 436/518
(58) Field of Classification Search .................. None
See application file for complete search history.

(56) References Cited

FOREIGN PATENT DOCUMENTS
WO       2005/105129 A2    11/2005

OTHER PUBLICATIONS

Aeschlimann, Daniel et al., "Protein Crosslinking in Assembly and Remodelling of Extracellular Matrices: The Role of Transglutaminases," *Connective Tissue Research* 41(1):1-27, 2000.

Aleanzi, Mabel et al., "Celiac Disease: Antibody Recognition against Native and Selectively Deamidated Gliadin Peptides," *Clinical Chemistry* 47(11):2023-2028, 2001.

Challacombe, D.N., "Screening tests for coeliac disease," *Archives of Disease in Childhood* 73:3-7, 1995.

Gentile, Vittorio et al., "Tissue transglutaminase and coeliac disease pathogenesis: potential molecular mechanisms for other human diseases," *Neurochemistry International* 40:79-83, 2002.

Kramer, Achim et al., *Methods in Molecular Biology, Combinatorial Peptide Library Protocols*, Humana Press, Totowa, New Jersey, 1998, Chapter 4, "Synthesis and Screening of Peptide Libraries on Continuous Cellulose Membrane Supports," pp. 25-39.

Molberg, Øyvind et al., "Tissue transglutaminase selectively modifies gliadin peptides that are recognized by gut-derived T cells in celiac disease," *Nature Medicine* 4(6):713-717, Jun. 1998.

Mothes, Thomas, "Deamidated Gliadin Peptides as Targets for Celiac Disease-Specific Antibodies," *Advances in Clinical Chemistry* 44:35-63, 2007.

Moyle, Peter M. et al., "Method for the Synthesis of Multi-Epitopic *Streptococcus pyogenes* Lipopeptide Vaccines Using Native Chemical Ligation," *J. Org. Chem.* 71(18):6846-6850, 2006.

Osman, A.A. et al., "B cell epitopes of gliadin," *Clinical and Experimental Immunology* 121:248-254, 2000.

Prause, C., et al., "Antibodies against deamidated gliadin peptides as highly valid biomarkers of childhood celiac disease," Poster Presentation at 22nd Congress of the Society for Pediatric Gastroenterology and Nutrition in Bochum, 2007.

Rönspeck, Wolfgang et al., "Peptide Based Adsorbers for Therapeutic Immunoadsorption," *Therapeutic Apheresis and Dialysis* 7(1):91-97, 2003.

Schwertz, Elke et al., "Serologic Assay Based on Gliadin-Related Nonapeptides as a Highly Sensitive and Specific Diagnostic Aid in Celiac Disease," *Clinical Chemistry* 50(12):2370-2375, 2004.

Sjöstrom, H. et al., "Identification of a Gliadin T-Cell Epitope in Coeliac Disease: General Importance of Gliadin Deamidation for Intestinal T-Cell Recognition," *Scand. J. Immunol.* 48:111-115, 1998.

*Primary Examiner* — Jacob Cheu
(74) *Attorney, Agent, or Firm* — SEED IP Law Group PLLC

(57) ABSTRACT

The present invention relates to fusion peptides that are derived from components of gliadin, to a method and reagents for the serological diagnosis of celiac disease or dermatitis herpetiformis by way of assaying antibodies that are directed against modified gliadin. The invention also relates to methods and pharmaceutical compositions for treating said diseases by specific immunoabsorption of these antibodies.

16 Claims, No Drawings

```
                               SEQUENCE LISTING

<160> NUMBER OF SEQ ID NOS: 11

<210> SEQ ID NO 1
<211> LENGTH: 16
<212> TYPE: PRT
<213> ORGANISM: Artificial Sequence
<220> FEATURE:
<223> OTHER INFORMATION: Peptide sequence D-2  according to Aleanzi
      et al. 2001. Clin Chem. 47:2023-2028

<400> SEQUENCE: 1

Gln Pro Glu Gln Pro Gln Gln Ser Phe Pro Glu Gln Glu Arg Pro Phe
1               5                   10                  15

<210> SEQ ID NO 2
<211> LENGTH: 9
<212> TYPE: PRT
<213> ORGANISM: Artificial Sequence
<220> FEATURE:
<223> OTHER INFORMATION: Nonapeptide sequence according to Schwertz
      et al. 2004. Clinical Chemistry 50:2370-2375

<400> SEQUENCE: 2

Pro Leu Gln Pro Glu Gln Pro Phe Pro
1               5

<210> SEQ ID NO 3
<211> LENGTH: 9
<212> TYPE: PRT
<213> ORGANISM: Artificial Sequence
<220> FEATURE:
<223> OTHER INFORMATION: Nonapeptide sequence according to Schwertz
      et al. 2004. Clinical Chemistry 50:2370-2375

<400> SEQUENCE: 3

Pro Glu Gln Leu Pro Gln Phe Glu Glu
1               5

<210> SEQ ID NO 4
<211> LENGTH: 17
<212> TYPE: PRT
<213> ORGANISM: Artificial Sequence
<220> FEATURE:
<223> OTHER INFORMATION: synthetic fusion peptide of SEQ ID NO:2 and
      SEQ ID NO:3

<400> SEQUENCE: 4

Pro Leu Gln Pro Glu Gln Pro Phe Pro Glu Gln Leu Pro Gln Phe Glu
1               5                   10                  15

Glu

<210> SEQ ID NO 5
```

```
<211> LENGTH: 198
<212> TYPE: DNA
<213> ORGANISM: Artificial Sequence
<220> FEATURE:
<223> OTHER INFORMATION: Three copies of the linker DNA made by
      hybridization of DNA oligonucleotides according to
      SEQ ID NO:10 and SEQ ID NO:11 are ligated in AdeI
      linearized pET24e vector DNA. The resulting coding
<220> FEATURE:
<223> OTHER INFORMATION: sequence for the protein according to SEQ ID
      NO:7 is shown

<400> SEQUENCE: 5
atggctcaca tgccgctgca gcctgaacaa ccatttcccg aacaactgcc gcagtttgaa      60
gaaatgccgc tgcagcctga caaccattt cccgaacaac tgccgcagtt tgaagaaatg     120
ccgctgcagc tgaacaacc atttcccgaa caactgccgc agtttgaaga aatggtgcac     180
caccaccacc accactga                                                   198

<210> SEQ ID NO 6
<211> LENGTH: 5401
<212> TYPE: DNA
<213> ORGANISM: E. coli
<220> FEATURE:
<223> OTHER INFORMATION: pET24e-GAF(3X) expression vector used as
      GAF(3X) peptide expression construct

<400> SEQUENCE: 6
ggggaattgt gagcggataa caattcccct ctagaaataa ttttgtttaa ctttaagaag      60
gagatatacc atggctcaca tgccgctgca gcctgaacaa ccatttcccg aacaactgcc     120
gcagtttgaa gaaatgccgc tgcagcctga caaccattt cccgaacaac tgccgcagtt     180
tgaagaaatg ccgctgcagc tgaacaacc atttcccgaa caactgccgc agtttgaaga     240
aatggtgcac caccaccacc accactgaga tccggctgct aacaaagccc gaaaggaagc     300
tgagttggct gctgccaccg ctgagcaata actagcataa ccccttgggg cctctaaacg     360
ggtcttgagg ggttttttgc tgaaaggagg aactatatcc ggattggcga atgggacgcg     420
ccctgtagcg gcgcattaag cgcggcgggt gtggtggtta cgcgcagcgt gaccgctaca     480
cttgccagcg ccctagcgcc cgctcctttc gctttcttcc cttcctttct cgccacgttc     540
gccggctttc cccgtcaagc tctaaatcgg ggctcccctt agggttccg atttagtgct     600 ttacggcacc tcgaccccaa aaaacttgat tagggtgatg gttcacgtgg gccatcgccc     660
tgatagacgg ttttcgccc tttgacgttg gagtccacgt tctttaatag tggactcttg     720
ttccaaactg gaacaacact caaccctatc tcggtctatt cttttgattt ataagggatt     780
ttgccgattt cggcctattg gttaaaaaat gagctgattt aacaaaaatt taacgcgaat     840
tttaacaaaa tattaacgtt tacaatttca ggtggcactt ttcggggaaa tgtgcgcgga     900
accctatttt gtttattttt ctaaatacat tcaaatatgt atccgctcat gaattaattc     960
ttagaaaaac tcatcgagca tcaaatgaaa ctgcaattta ttcatatcag gattatcaat    1020
accatatttt tgaaaagcc gtttctgtaa tgaaggagaa aactcaccga ggcagttcca     1080
taggatggca agatcctggt atcggtctgc gattccgact cgtccaacat caatacaacc    1140
tattaatttc ccctcgtcaa aaataaggtt atcaagtgag aaatcaccat gagtgacgac    1200
tgaatccggt gagaatggca aaagttatg catttctttc cagacttgtt caacaggcca    1260
gccattacgc tcgtcatcaa atcactcgc atcaaccaaa ccgttattca ttcgtgattg    1320
cgcctgagcg agacgaaata cgcgatcgct gttaaaagga caattacaaa caggaatcga    1380
atgcaaccgg cgcaggaaca ctgccagcgc atcaacaata ttttcacctg aatcaggata    1440
```

```
ttcttctaat acctggaatg ctgttttccc ggggatcgca gtggtgagta accatgcatc    1500
atcaggagta cggataaaat gcttgatggt cggaagaggc ataaattccg tcagccagtt    1560
tagtctgacc atctcatctg taacatcatt ggcaacgcta cctttgccat gtttcagaaa    1620
caactctggc gcatcgggct tcccatacaa tcgatagatt gtcgcacctg attgcccgac    1680
attatcgcga gcccatttat acccatataa atcagcatcc atgttggaat ttaatcgcgg    1740
cctagagcaa gacgtttccc gttgaatatg gctcataaca ccccttgtat tactgtttat    1800
gtaagcagac agttttattg ttcatgacca aaatccctta acgtgagttt tcgttccact    1860
gagcgtcaga ccccgtagaa aagatcaaag gatcttcttg agatcctttt tttctgcgcg    1920
taatctgctg cttgcaaaca aaaaaaccac cgctaccagc ggtggtttgt ttgccggatc    1980
aagagctacc aactctttt ccgaaggtaa ctggcttcag cagagcgcag ataccaaata    2040
ctgtccttct agtgtagccg tagttaggcc accacttcaa gaactctgta gcaccgccta    2100
catacctcgc tctgctaatc ctgttaccag tggctgctgc cagtggcgat aagtcgtgtc    2160
ttaccgggtt ggactcaaga cgatagttac cggataaggc gcagcggtcg ggctgaacgg    2220
ggggttcgtg cacacagccc agcttggagc gaacgaccta caccgaactg agatacctac    2280
agcgtgagct atgagaaagc gccacgcttc ccgaagggag aaaggcggac aggtatccgg    2340
taagcggcag ggtcggaaca ggagagcgca cgagggagct tccaggggga aacgcctggt    2400
atctttatag tcctgtcggg tttcgccacc tctgacttga gcgtcgattt ttgtgatgct    2460
cgtcaggggg gcggagccta tggaaaaacg ccagcaacgc ggcctttta cggttcctgg    2520 ccttttgctg gccttttgct cacatgttct ttcctgcgtt atccctgat tctgtggata    2580 accgtattac cgcctttgag tgagctgata ccgctcgccg cagccgaacg accgagcgca    2640
gcgagtcagt gagcgaggaa gcggaagagc gcctgatgcg gtattttctc cttacgcatc    2700
tgtgcggtat ttcacaccgc atatatggtg cactctcagt acaatctgct ctgatgccgc    2760
atagttaagc cagtatacac tccgctatcg ctacgtgact gggtcatggc tgcgccccga    2820
cacccgccaa cacccgctga cgcgccctga cgggcttgtc tgctcccggc atccgcttac    2880
agacaagctg tgaccgtctc cgggagctgc atgtgtcaga ggttttcacc gtcatcaccg    2940
aaacgcgcga ggcagctgcg gtaaagctca tcagcgtggt cgtgaagcga ttcacagatg    3000
tctgcctgtt catccgcgtc cagctcgttg agtttctcca gaagcgttaa tgtctggctt    3060
ctgataaagc gggccatgtt aagggcggtt ttttcctgtt tggtcactga tgcctccgtg    3120
taagggggat ttctgttcat gggggtaatg ataccgatga acgagagag gatgctcacg    3180 atacggggtta ctgatgatga acatgcccgg ttactggaac gttgtgaggg taaacaactg    3240
gcggtatgga tgcggcggga ccagagaaaa atcactcagg gtcaatgcca gcgcttcgtt    3300
aatacagatg taggtgttcc acagggtagc cagcagcatc ctgcgatgca gatccggaac    3360
ataatggtgc agggcgctga cttccgcgtt tccagacttt acgaaacacg gaaaccgaag    3420
accattcatg ttgttgctca ggtcgcagac gttttgcagc agcagtcgct tcacgttcgc    3480
tcgcgtatcg gtgattcatt ctgctaacca gtaaggcaac cccgccagcc tagccgggtc    3540
ctcaacgaca ggagcacgat catgcgcacc cgtggggccg ccatgccggc gataatggcc    3600
tgcttctcgc cgaaacgttt ggtggcggga ccagtgacga aggcttgagc gagggcgtgc    3660
aagattccga ataccgcaag cgacaggccg atcatcgtcg cgctccagcg aaagcggtcc    3720
tcgccgaaaa tgacccagag cgctgccggc acctgtccta cgagttgcat gataaagaag    3780
acagtcataa gtgcggcgac gatagtcatg ccccgcgccc accggaagga gctgactggg    3840
```

-continued

```
ttgaaggctc tcaagggcat cggtcgagat cccggtgcct aatgagtgag ctaacttaca    3900
ttaattgcgt tgcgctcact gcccgctttc cagtcgggaa acctgtcgtg ccagctgcat    3960
taatgaatcg gccaacgcgc ggggagaggc ggtttgcgta ttgggcgcca gggtggtttt    4020
tcttttcacc agtgagacgg gcaacagctg attgcccttc accgcctggc cctgagagag    4080
ttgcagcaag cggtccacgc tggttttgcc cagcaggcga aaatcctgtt tgatggtggt    4140
taacggcggg atataacatg agctgtcttc ggtatcgtcg tatcccacta ccgagatatc    4200
cgcaccaacg cgcagcccgg actcggtaat ggcgcgcatt gcgcccagcg ccatctgatc    4260
gttggcaacc agcatcgcag tgggaacgat gccctcattc agcatttgca tggtttgttg    4320
aaaaccggac atggcactcc agtcgccttc ccgttccgct atcggctgaa tttgattgcg    4380
agtgagatat ttatgccagc cagccagacg cagacgcgcc gagacagaac ttaatgggcc    4440
cgctaacagc gcgatttgct ggtgacccaa tgcgaccaga tgctccacgc ccagtcgcgt    4500
accgtcttca tgggagaaaa taatactgtt gatgggtgtc tggtcagaga catcaagaaa    4560
taacgccgga acattagtgc aggcagcttc cacagcaatg gcatcctggt catccagcgg    4620
atagttaatg atcagcccac tgacgcgttg cgcgagaaga ttgtgcaccg ccgctttaca    4680
ggcttcgacg ccgcttcgtt ctaccatcga caccaccacg ctggcaccca gttgatcggc    4740
gcgagattta atcgccgcga caatttgcga cggcgcgtgc agggcagac tggaggtggc    4800
aacgccaatc agcaacgact gtttgcccgc cagttgttgt gccacgcggt tgggaatgta    4860
attcagctcc gccatcgccg cttccacttt ttcccgcgtt ttcgcagaaa cgtggctggc    4920
ctggttcacc acgcgggaaa cggtctgata agagacaccg gcatactctg cgacatcgta    4980
taacgttact ggtttcacat tcaccaccct gaattgactc tcttccgggc gctatcatgc    5040
cataccgcga aaggttttgc gccattcgat ggtgtccggg atctcgacgc tctcccttat    5100
gcgactcctg cattaggaag cagcccagta gtaggttgag gccgttgagc accgccgccg    5160
caaggaatgg tgcatgcaag gagatggcgc ccaacagtcc cccggccacg gggcctgcca    5220
ccatacccac gccgaaacaa cgctcatga gcccgaagtg gcgagcccga tcttccccat    5280
cggtgatgtc ggcgatatag cgccagcaa ccgcacctgt ggcgccggtg atgccggcca    5340
cgatgcgtcc ggcgtagagg atcgagatct cgatcccgcg aaattaatac gactcactat    5400
a                                                                    5401
```

<210> SEQ ID NO 7
<211> LENGTH: 65
<212> TYPE: PRT
<213> ORGANISM: Artificial Sequence
<220> FEATURE:
<223> OTHER INFORMATION: Recombinant fusion protein containing a C-
      terminal hexa-histidine-Tag for protein purification and
      three copies of the Gliadin analogue synthetic
      sequence according to SEQ ID NO:4 interspaced with
<220> FEATURE:
<223> OTHER INFORMATION: a single methionine residue

<400> SEQUENCE: 7

Met Ala His Met Pro Leu Gln Pro Glu Gln Pro Phe Pro Glu Gln Leu
 1               5                  10                  15

Pro Gln Phe Glu Glu Met Pro Leu Gln Pro Glu Gln Pro Phe Pro Glu
                20                  25                  30

Gln Leu Pro Gln Phe Glu Glu Met Pro Leu Gln Pro Glu Gln Pro Phe
            35                  40                  45

Pro Glu Gln Leu Pro Gln Phe Glu Glu Met Val His His His His His

```
<210> SEQ ID NO 8
<211> LENGTH: 36
<212> TYPE: DNA
<213> ORGANISM: Artificial Sequence
<220> FEATURE:
<223> OTHER INFORMATION: Chemically synthesized DNA oligonucleotide
      primer used to amplify pET24e-fragment by PCR

<400> SEQUENCE: 8
ctcacatggt gcaccaccac caccaccact gagatc                              36

<210> SEQ ID NO 9
<211> LENGTH: 44
<212> TYPE: DNA
<213> ORGANISM: Artificial Sequence
<220> FEATURE:
<223> OTHER INFORMATION: Chemically synthesized DNA oligonucleotide
      primer used to amplify the pET24e-fragment by PCR

<400> SEQUENCE: 9
gtgcaccatg tgagccatgg tatatctcct tcttaaagtt aaac                     44

<210> SEQ ID NO 10
<211> LENGTH: 54
<212> TYPE: DNA
<213> ORGANISM: Artificial Sequence
<220> FEATURE:
<223> OTHER INFORMATION: 5'-phosphorylated chemically synthesized
      sense DNA oligonucleotide that hybridizes with DNA
      oligonucleotide according to SEQ ID NO:11 to form
      the linker to be inserted in AdeI linearized
<220> FEATURE:
<223> OTHER INFORMATION: pET24e

<400> SEQUENCE: 10
ccgctgcagc ctgaacaacc atttcccgaa caactgccgc agtttgaaga aatg          54

<210> SEQ ID NO 11
<211> LENGTH: 54
<212> TYPE: DNA
<213> ORGANISM: Artificial Sequence
<220> FEATURE:
<223> OTHER INFORMATION: 5'-phosphorylated chemically synthesized
      antisense DNA oligonucleotide that hybridizes with DNA
      oligonucleotide according to SEQ ID NO:10 to form
      the linker to be inserted in AdeI linearized
<220> FEATURE:
<223> OTHER INFORMATION: pET24e

<400> SEQUENCE: 11
ttcttcaaac tgcggcagtt gttcgggaaa tggttgttca ggctgcagcg gcat          54
```

METHOD AND IMMUNOABSORBENTS FOR SPECIFIC DETECTION AND ABSORPTION OF ANTIBODIES ASSOCIATED WITH CELIAC DISEASE AND DERMATITIS HERPETIFORMIS

STATEMENT REGARDING SEQUENCE LISTING

The Sequence Listing associated with this application is provided in text format in lieu of a paper copy, and is hereby incorporated by reference into the specification. The name of the text file containing the Sequence Listing is 310159_403USPCa_SEQUENCE_LISTING.txt. The text file is 11 KB, was created on Apr. 20, 2010, and is being submitted electronically via EFS-Web.

The present invention relates to fusion peptides that are derived from components of gliadin, test reagents for the diagnostic detection of antibodies against said peptides and methods for the immunoabsorption of said antibodies for the therapy of celiac disease and dermatitis herpetiformis.

STATE OF THE ART

Consumption of gluten-containing cereal products leads to damage of the mucosa of the small intestine in patients with intolerance to gluten (gluten-sensitive enteropathy; infants and children: celiac disease, adults: endemic sprue; in the present application, the term "celiac disease" will be used age-independently and synonymous to gluten-sensitive enteropathy). This results in villous atrophy and malfunction. The clinical symptoms are dominated by diarrhea and the consequences of malabsorption (in particular, weight loss, growth retardation in children). Some patients with gluten-sensitive enteropathy additionally develop dermatitis herpetiformis, or Duhring's disease, a chronic blistering skin condition which, however, may also arise independently.

An important contribution to the diagnosis of gluten-sensitive enteropathy and dermatitis herpetiformis is provided by the analysis of two different antibodies, to gliadin and to tissue transglutaminase. It confirms the clinical diagnosis and is also well suited for the monitoring of disease progression and for controlling gluten-free diet or a gluten stress test. A specific separation of these two antibodies from the patients' plasma can be associated with a positive therapeutic effect.

During the active disease phase of gluten-sensitive enteropathy as well as in dermatitis herpetiformis, gliadin antibodies of the IgA and IgG class are detectable most of the time. Antibodies of the IgM class are occasionally also detectable, as a rule, however, only in the presence of gliadin antibodies of the IgA and IgG class.

With the start of a gluten-free diet, IgA antibodies to gluten drop to lower values within a couple of months, whereas the IgG class antibodies generally persist longer. Permanently high levels of IgA gliadin antibodies indicate that a gluten-fee diet is not complied with. Under gluten stress in the event of relapse, the IgG antibodies to gliadin rise within a few days, the IgA antibodies following somewhat later.

The physiological function of tissue transglutaminase is in cross linking of extracellular matrix proteins by catalyzing the formation of an iso-peptide bond between a γ-carboxamide group of a glutamine residue and an ε-amino group of a lysine residue (Aeschlimann et al. 2000 Connective Tissue Res. 41:1-27; Gentile et al. 2002. Neurochem Int. 40:79-83).

Glutamine-rich gliadins taken up from food can also be modified by tissue transglutaminase after resorption. However, here, preferably, the enzymatic deamination from glutamine to glutamic acid residues takes place (summarized in Schwertz et al. 2004. Clin Chem. 50:2370-2375). This results in a stronger binding of gliadin peptides to MHC class II molecules and, as a consequence, an increased T cell stimulation in patients with celiac disease (Sjöström et al. 1998. Scand J Gastroenterol. 48:111-115; Molberg et al. 1998. Nat Med. 4:713-717).

The tripeptide proline—glutamic acid—glutamine (PEQ) was identified as an important epitope, in particular of parts of deaminated gliadin, for antibodies of the IgA class (Osman et al. 2000. Clin. Exp. Immunol. 121:248-254). It was demonstrated that deaminated gliadin is more specifically recognized by antibodies of celiac disease patients than unmodified gliadin (Aleanzi et al. 2001. Clin. Chem. 47:2023-2028). For the detection of antibodies to a deaminated peptide derived from gliadin in celiac disease as an indicator of celiac disease, the authors determined a sensitivity of 85.0% with a specificity of 86.7% for antibodies of the IgA class, and a sensitivity of 90.0% with a specificity of 86.7% for antibodies of the IgG class (cf. Table 1, a).

In the context of a systematic analysis of the binding of celiac disease-associated antibodies of the IgA class to synthetic antigens preferably derived from gliadin, two nonapeptides with the sequences SEQ-ID NO 2 (Pro Leu Gln Pro Glu Gln Pro Phe Pro) and SEQ-ID NO 3 (Pro Glu Gln Leu Pro Gln Phe Glu Glu) were identified as most suitable antigens (Schwertz et al. 2004 Clin. Chem. 50:2370-2375). The two peptides (according to Kramer et al. 1998. J. Methods Mol. Biol. 87:25-39) were chemically synthesized separately and in parallel on a cellulose membrane, which was subsequently directly used for the binding of celiac disease-associated antibodies in a chemiluminescence test. The method is known from the manufacturing of membrane-based peptide banks in the context of epitope mapping studies. Respective reagents for the detection of antibody lead to high production costs for the manufacturing of diagnostic test systems.

Nevertheless, Schwertz et al. have carried out two membrane-based ELISA tests using chemiluminescence detection for the detection of the IgA class antibodies to gliadin in celiac disease, which in a combined analysis of both antigens according to sequences SEQ ID NO:2 and SEQ ID NO:3 (Table 1, b) resulted in a sensitivity of 94.2% with a specificity of 93.4%.

Chemiluminescence detection is laborious and dependent on expensive analyzing machines. It has not been shown whether the performance data obtained could also be achieved with the far more wide-spread colorimetric detection methods. The authors themselves point out this disadvantage and for further improvement propose a further sequence optimization as well as the transfer of the membrane-based chemiluminescence test system into the microtiter plate format, without actually solving this task.

Schwertz et al. have only included tissue transglutaminase-IgA positive sera in the study. In the Schwertz et al. study, samples from patients with selective IgA deficiency did not lead to a decrease in sensitivity, as in an open selection of patients, so that an unjustified exceedingly high sensitivity in the range of 3-5% is to be expected here. Furthermore, the performance data are based on a combined analysis of two separate determinations based on the peptide sequences of SEQ ID NO:2 and SEQ ID NO:3, which are only poorly suitable for routine testing.

In a study (Prause et al. 2007, poster presentation at the 22nd Congress of the Society for pediatric gastroenterology and nutrition in Bochum), a microtiter plate-based ELISA for detecting antibodies of the IgG class on the basis of one of the two nonapeptides (according to sequence SEQ ID NO:2) also showed an improvement over the state of the art for the determination of antibodies of the IgG class; no results were presented for IgA (cf. Table 1, c).

It was shown in the study of Schwertz et al. that the antibody determination using the peptides according to SEQ ID NO:2 and SEQ ID NO:3, which was conducted separately, but analyzed together, allows an improvement of the serological diagnosis of celiac disease. The performance in the work of Aleanzi et al. was clearly exceeded by Schwertz et al. However, according to Schwertz et al., at least two independent syntheses and determinations (antigens according to SEQ ID NO:2 and SEQ ID NO:3) must be conducted separately, resulting in a doubled expenditure of material and work. It would be possible to mix the two peptide antigens and to use the mixture for the coating of the solid phase in ELISA. Such tests, however, suffer from lack of reproducibility, an increase in unspecific reactions and mutual steric hindrance in the binding of the antigen components to the surface.

TABLE 1

Synopsis of the published performance data of test systems based on peptide antigens homologous to deaminated gliadin.

|   | Immunoglobulin class | Sensitivity | Specificity | Source |
|---|---|---|---|---|
| a | IgA | 85.0% | 86.7% | Aleanzi et al., 2001 |
|   | IgG | 90.0% | 86.7% | SEQ ID NO: 1 |
| b* | IgA | ≦94.2% | 93.4% | Schwertz et al., 2004 |
|   | IgG | not sufficient? | not sufficient? | SEQ ID NO: 2 and SEQ ID NO: 3 |
| c | IgA | not sufficient? | not sufficient? | Prause et al., 2007 |
|   | IgG | 95.0% | 94.7% | SEQ ID NO: 2 |

*incorrect pre-selected patient selection

The task of the invention was to overcome the disadvantages of the state of the art described supra and to provide a better antibody test system for the diagnosis of celiac disease which provides competent results and is suitable for routine testing.

DESCRIPTION OF THE INVENTION

This task is solved by the subject matter of the claims, in particular by the fusion polypeptide described below.

It can be derived from the sate of the art that a competent diagnosis of celiac disease is possible using the individual peptides with sequences SEQ ID NO:2 and SEQ ID NO:3. Accordingly, we first chemically synthesized these two peptides in biotinylated form and used them for the coating of microtiter plates. By determining bound biotin, it could be ensured that the peptides have attached to the surface; however, it was not possible to reproduce the diagnostic performance parameters derived from the prior art. Thereupon, we stopped the experiments with the chemically synthesized peptides according to SEQ ID NO:2 and SEQ ID NO:3.

As an alternative to chemical synthesis, it would have been possible to express the peptides according to SEQ ID NO:2 and SEQ ID NO:3 recombinantly (cf. Examples 1 and 2), in form of multiple fused copies separated from each other by methionine residues that could be cleaved into individual peptides by cyanogen bromide. One would then have separated the components, conducted individual ELISA tests, and used them either in parallel for the diagnosis, or as a mixture for the coating.

The inventors however have pursued the idea to combine the peptides according to SEQ ID NO:2 and SEQ ID NO:3 into a new fusion peptide with the sequence SEQ ID NO:4 (Pro Leu Gln Pro Glu Gln Pro Phe Pro Glu Gln Leu Pro Gln Phe Glu Glu). Multiple copies of this fusion peptide fused together were to be synthesized and, after recombinant synthesis, cleaved into individual peptides. We synthesized a corresponding DNA and integrated it in trimeric form into an E. coli expression plasmid, so that we obtained the circular plasmid according to SEQ ID NO:6 (cf. Example 1). Using this plasmid, we could express the polypeptide according to SEQ ID NO:7 (hereinafter referred to as trimer) in E. coli, isolate it (cf. Example 2) and—as expected—subsequently cleave it by treatment with cyanogen bromide. The cleavage product (monomer) was used for the coating of microtiter plates. In parallel, we carried out controls with the uncleaved trimer under identical conditions. Unexpectedly, in the ELISA with colorimetric detection (cf. Example 3), we achieved significantly better performance data with the trimer as antigen substrate for the IgG immunoglobulin class, for the identification of the celiac disease patients than with test systems of the already highly developed state of the art (cf. Table 2).

In preliminary tests, even with monomers obtained by cleavage of the trimer, the performance data of the ELISA system from the state of the art could already be superseded. The by far best results were, however, achieved with the uncleaved trimer. Peptide antigens made up from more than three polypeptide sequences according to SEQ ID NO:4 can also provide excellent performance data.

To determine the performance data of the ELISA based on the polypeptide according to SEQ ID NO:7 (trimer), we subsequently carried out a study with serum samples from persons with bioptically confirmed positive or negative diagnosis of celiac disease (cf. Example 3). In contrast to Schwertz et al., the collective was not pre-selected, i.e., patients with selective IgA deficiency were not excluded. The collective was composed as follows:

Group 1: Celiac disease patients without a special diet at the time point of the biopsy (Marsh 2-3). This group also encompasses patients with dermatitis herpetiformis.

Group 2: Patients with dermatitis herpetiformis without known celiac disease.

Group 3: Patients whose bioptic examination indicates there is no celiac disease (Marsh 0).

Group 4: Patients with chronic inflammatory gut diseases (Crohn's disease and ulcerative colitis), whose small intestine was bioptically examined, and no alterations typical for celiac disease were described.

For the determination of the performance parameters by signal analysis by means of "receiver operating characteristic" curves (ROC) analysis, group 1 was used as clinically confirmed celiac disease positive group, group 2 as clinically confirmed dermatitis herpetiformis positive group, and groups 3 and 4 as negative control groups.

Results: As depicted in Table 2, the ELISA based on the polypeptide according to SEQ ID NO:7 was found to exhibit higher sensitivity and specificity for the detection of celiac disease specific antibodies of the IgG class than the test described by Prause et al. Furthermore, a high quality determination of antibodies of the IgA class is also possible with the same ELISA of the invention.

We could show that by combining the peptide sequences SEQ ID NO:2 and SEQ ID NO:3 in one peptide according to sequence SEQ ID NO:7, antigens can be produced that are suitable as substrates for robust, easy-to-produce ELISA with colorimetric detection. Compared to the state of the art, test systems comprising the antigen substrates of the invention can be used for easier, more reliable and more precise determination of celiac disease associated antibodies. The method of the invention furthermore also allows the specific determination of antibodies of the IgA and IgG class in patients with dermatitis herpetiformis (cf. Table 2).

TABLE 2

Performance parameter of the ELISA of the invention relating to the diagnosis of celiac disease and an isolated dermatitis herpetiformis.

|  |  | Sensitivity | Specificity |
|---|---|---|---|
| celiac disease | IgA | 80.8% | 94.6% |
|  | IgG | 98.0% | 96.0% |
| dermatitis herpetiformis | IgA | 66.7% | 94.6% |
|  | IgG | 66.7% | 96.0% |

With respect to the diagnosis of celiac disease, we achieved a sensitivity of 98.0% with a specificity of 96.0% with a reagent according to the invention (variant SEQ ID NO:7, trimer), for the detection of celiac disease associated antibodies of the IgG class. These values significantly exceed the best data published so far (Prause et al.: sensitivity 95.0%, specificity 94.7%).

With regard to antigens of the IgA class, the sensitivity is 80.8%, and thus is lower than in the data published by Aleanzi et al. and Schwertz et al. (cf. Tables 1, a and b). Aleanzi et al. have, however, achieved an insufficient specificity of 86.7%, and their data is therefore comparable with our results with respect to IgA, when specificity and sensitivity are taken together. The values of Schwertz et al. can only conditionally be used for the comparison, because the patient collective was pre-selected. The exclusion of patient samples with selective IgA deficiency in the studies by Schwertz et al. (about 3% of patients with celiac disease; Challacombe et al. 1995, Arch. Dis. Childhood 73:3-7; cf. note to Table 1) leads to an seemingly high diagnostic sensitivity which cannot be reproduced in a collective without pre-selection. Moreover, the test system of Schwertz et al. is not applicable in industrial production.

The superiority of one of the target antigens of the invention over the state of the art has clearly been confirmed for the IgG class immunoglobulins. As experience shows that in celiac disease and dermatitis herpetiformis, the IgA and IgG class antibodies to gliadin are directed against the same antigenic epitopes, it can be assumed that when using the sample material from identical patient collectives in the test systems of the state of the art and the present invention for the determination of IgA, the best performance parameters can be identified for the latter system.

Antigens of the invention can be produced by technically simple ways and in sufficient amounts and best quality. Without further ado, they can be bound to defined surfaces. They are suitable, among others, but not exclusively, for solid phase immune tests and therapeutic methods involving immunoaffinity chromatography.

The invention is directed to fusion polypeptides comprising peptides sequences according to SEQ ID NO:2 and SEQ ID NO:3 in any sequential order. Therein, up to 30% of the amino acids can be removed or exchanged against arbitrary amino acids at any place, wherein the activity of the fusion polypeptides is to remain comparable, in particular, the binding to antibodies specific for celiac disease and dermatitis herpetiformis. Specifically, the fusion polypeptide may comprise one, two, three, four or five amino acid substitutions, in particular, conservative amino acid substitutions, or deletions (distributed between both sequences, in particular one, two or three amino acid substitutions or deletions per sequence).

Of course, the fusion polypeptide can also contain further sequences. In one embodiment, more than 50% of the peptide is attributed to one of the sequences according to SEQ ID NO:2 or SEQ ID NO:3. Specifically, up to 30% or 40% of arbitrary amino acids can be added. These amino acids can provide for, e.g., easier purification of the peptide (e.g., His-Tag, Flag-Tag etc.), better stability or better accessibility for antibodies (e.g., as spacer between the epitope sequences). Of course, further epitopes useful for the diagnosis or therapy of celiac disease and/or dermatitis herpetiformis, for example, from tissue transglutaminase, can also be comprised.

Alternatively, the fusion polypeptides may contain only one copy of the respective peptide sequences, in particular, however, they comprise peptide sequences according to SEQ ID NO:2 and SEQ ID NO:3, i.e., a plurality of copies of each. Such fusion polypeptides preferably comprise two or more, in particular three or more or three to twenty or four to ten copies of the respective sequence. Therein, the number of copies of SEQ ID NO:2 and SEQ ID NO:3 may be equal or different, and the sequences may partially overlap, but do not need to. For example, two copies of SEQ ID NO:2 and three copies of SEQ ID NO:3 or vice versa may be present.

The smallest unit of the preferred polypeptides of the invention contains the peptides described by Schwertz et al. according to SEQ ID NO:2 and SEQ ID NO:3 in an overlapping sequence according to SEQ ID NO:4.

Therefore, compared to Schwertz et al. there is no need to conduct two tests in parallel. Multimeric forms of the unit of the invention, in particular the smallest unit, offer higher security than monomeric forms after they have been linked to a surface, because a sufficient number of epitopes is available for the reaction with the specific antibodies, and some epitopes are still left when parts of the polypeptide have become inaccessible for the binding reaction to the surface.

The qualitative advance over the state of the art achieved in the present invention is probably the highest in the new peptide sequences according to SEQ ID NO:4 or SEQ ID NO:7. These peptide sequences are to be regarded as a new quality over the state of the art. The invention is also directed to polypeptides with more or less than three copies of the peptide according to SEQ ID NO:4, in particular with two or more, three or more or four or more copies, as well as to partial peptides consisting of at least 10, at least 14, at least 15 or at least 16 successive amino acids of SEQ ID NO:4, as these can be used like the polypeptide according to SEQ ID NO:7, and preferably show a comparable binding of the antibodies.

The invention is further directed to fusion polypeptides made up from any sequence and number of combined polypeptides according to SEQ ID NO:2 and SEQ ID NO:3, with as well as without sequence overlap, as, here, too, binding properties comparable to the fusion polypeptide according to SEQ ID NO:4 are expected for binding to antibodies specific to celiac disease and dermatitis herpetiformis.

The skilled person knows that physicochemically similar derivatives can be generated from the polypeptides described supra by one or more conservative amino acid substitutions (glutamic acid to aspartic acid E->D, glutamine to asparagine Q->N, phenylalanine to tyrosine F->Y, leucine to isoleucine L->I) at any position. Such derivatives are also subject matter of the invention and are enclosed within the scope of the invention, because comparable properties with respect to binding of antibodies specific for celiac disease and/or dermatitis herpetiformis are expected. The skilled person understands that comparable properties refer to a similar specificity and sensitivity, in particular for the diagnostic detection of celiac disease and/or dermatitis herpetiformis as depicted in Table 2 for the detection of IgA and/or IgG (−2% or better, or, preferably, −1% or better), in particular, the binding of antibodies is also comparable to the binding to the fusion polypeptide according to SEQ ID NO:7. In particular, up to 10%, up to 20% or up to 30% of the amino acids can be exchanged by one or more conservative amino acid substitutions, wherein the binding of antibodies specific for celiac disease and/or dermatitis herpetiformis is comparable.

In a preferred embodiment, a polypeptide of the invention contains at least one and at most twenty copies of the sequence according to SEQ ID NO:4. In a particularly preferred embodiment, a polypeptide of the invention contains at least two and at most ten copies of the sequence according to SEQ ID NO:4 or at least three copies of the sequence according to SEQ ID NO:4. In an alternative embodiment, a mixture of various polypeptides of the invention is used.

The fusion polypeptides of the invention can also be present in form of polymers, in particular polymers comprising two to twenty or three to ten fusion polypeptides of the invention. It is not necessary that they are linked by a peptide bond; rather they can be covalently linked by other means (e.g., over a linker group) or be associated in a non-covalent manner.

The skilled person is aware of other methods for producing, purifying and isolating the recombinant polypeptides of the invention, whether with or without fusion partners, such as filtration, chromatography, electrophoresis, centrifugation methods or a combination of those. Such methods for the purification of proteins are described, for example, in Lottspeich and Zorbas (Bioanalytik, 1998, Spektrum akademischer Verlag, Heidelberg, Berlin) or Sambrook et al. (Molecular cloning: a laboratory manual, 2000, Cold Spring Harbor Laboratory Press, Cold Spring Harbor, N.Y.). The invention is therefore also directed to polypeptides of the invention that are produced, purified or isolated using such methods. In a preferred embodiment, the polypeptide of the invention is recombinantly produced in E. coli.

Accordingly, the invention is also directed to also nucleic acids (DNA or RNA) which encode one or more fusion polypeptides of the invention, e.g., a polypeptide comprising the peptide according to SEQ ID NO:4 or SEQ ID NO:7. These nucleic acids can be present in an expression vector under the control of a heterologous promoter. The expression vector can be within a host cell. It was found that, e.g., E. coli is suitable for the expression of the fusion polypeptides of the invention.

The invention is also directed to polypeptides of the invention labeled with a reporter molecule. The skilled person is well aware of a number of different chemical coupling methods such as a method first involving attachment of a reactive group, for example, pentafluorophenyl ester, N-hydroxysuccinimide or maleimide, to the reporter molecule, and bringing the resultant activated reporter molecules in contact with the target molecule to be labeled, for example, an antigen or a protein. After coupling of the reporter molecule to the target molecule, excess reporter molecules can be removed by chemical, biochemical or physical separation techniques, for example, chromatography or filtration. The skilled person knows various compounds as reporter molecules, such as fluorophores, e.g., fluorescein or tetramethyl-rhodamine, haptens, e.g., biotin or His-Tag and enzymes, e.g., horseradish peroxidase or alkaline phosphates. Activated reporter molecules are commercially available for the use in the various coupling methods. The skilled person knows further reporter molecules and coupling methods for labeling proteins. The invention is thus also directed to polypeptides of the invention that are produced by these methods and labeled with reporter molecules.

Fusion polypeptides of the invention that are directly or indirectly bound to a solid phase (e.g., a plastic carrier such as a microtiter plate, a magnetic bead, a membrane, e.g., a nitrocellulose membrane) are also subject matter of the invention.

The invention is also directed to methods for the diagnosis of celiac disease and/or dermatitis herpetiformis wherein a liquid biological sample from a patient (in particular blood, plasma or a stool probe optionally diluted with water or a suitable buffer) is brought in contact with polypeptides of the invention, and the binding of antibodies from this biological sample to the polypeptides takes place or can take place, wherein celiac disease or dermatitis herpetiformis is diagnosed by detection of said antibodies to one of said polypeptides. A mixture of at least two polypeptides of the invention can be used in these methods.

In the context of the invention, it was found that the polypeptides of the invention are particularly suitable for conducting immunological methods such as Western blot, line blot, dot blot or immunofluorescence tests. The invention is therefore also directed to such methods or diagnostic methods, wherein binding of the antibodies is detected using an immunofluorescence test, microarray, ELISA, luminescence test, blot, radioimmune test, Western blot or dot blot.

The invention also provides a test kit for the detection of antibodies comprising one or more fusion polypeptides of the invention. This kit allows, for example, to perform a diagnostic method of the invention. Such a test kit may also comprise secondary antibodies, e.g., anti-human IgA and/or anti-human IgG antibodies that can optionally be labeled with a reporter molecule. In one embodiment, the test kit further comprises antigens which are also suitable for the diagnosis of celiac disease and/or dermatitis herpetiformis, such as tissue transglutaminase or a polypeptide comprising epitopes from this that are suitable for the diagnosis. Therefore, the test kit can be used, e.g., for a combined test in which IgA antibodies to tissue transglutaminase and IgG antibodies to the polypeptides of the invention are detected.

The invention is also directed to therapeutic methods for the removal of antibodies specific for celiac disease from blood or plasma, preferably of patients with celiac disease and dermatitis herpetiformis. This can be done, for example, by ex vivo immunoabsorption (immune apheresis) on immobilized polypeptides of the invention (according to Example 4). Through the contact with the blood or plasma, the antibodies specific for the immobilized polypeptides are removed and the depleted body fluids can subsequently be reinfused. Respective methods are described, e.g., for the therapy of dilated cardiomyopathy based on the sequence of the beta adrenergic receptor (Ronspeck et al. 2003 Ther. Apher. Dial. 7:91-97). In a preferred embodiment, a polypeptide according to SEQ ID NO:7 is immobilized on a solid matrix by chemical linkage and used as a basis for an immune test or a therapeutic immunoaffinity chromatography absorption method.

The invention hence provides a method for the therapy of celiac disease and/or dermatitis herpetiformis wherein blood or plasma of a patient is brought in contact with one or more polypeptides of the invention bound to a solid phase, the disease-associated antibodies from the blood or plasma bind to these polypeptides, wherein the antibody-depleted blood or plasma is suitable for the reinfusion into the patient. In one embodiment, the fusion polypeptides of the invention are herein used in combination with polypeptides comprising epitopes of tissue transglutaminase.

The invention further concerns the use of one or more fusion polypeptides described for the preparation of a pharmaceutical composition, in particular for the therapy of celiac disease and/or dermatitis herpetiformis. This pharmaceutical composition is in particular suitable for the binding/absorption of antibodies of different antibody classes (IgA, IgG) from the patient blood or plasma.

EXAMPLE 1

Cloning of pET24e-(Gliadin-rd)$_3$

Preparation of the Vector Fragment:
First, the unique AdeI restriction site in the plasmid pET24d (Novagen) was destroyed. After linearization of the pET24d plasmid with AdeI, the removal of the 3' single strand overhangs was catalyzed by PfU polymerase (Fermentas) in the absence of dNTPs. Then, religation of the vector fragments by T4 DNA ligase followed. This plasmid DNA was subsequently amplified using the DNA oligonucleotide primers sense pET24e (SEQ ID NO:8) and antisense pET24e (SEQ ID NO:9), and the pET24e vector fragment obtained after AdeI digestion and dephosphorylation of the 5' ends was used for the integration of the synthetic DNA sequence derived from the partially deaminated gliadin.

Using 5' the phosphorylated DNA oligonucleotides sense dpGlia (SEQ ID NO:10) and antisense dpGlia (SEQ ID NO:11), a linker sequence was generated which exhibits the AdeI compatible 5' phosphorylated overhangs which allow a directed ligation into the AdeI-digested and dephosphorylated pET24e vector fragment using T4 DNA ligase (Fermentas).

The hybridization of the linker was carried out in 50 μl reaction volume of the following composition:
75 mM Tris-HCl (pH 8.8 at 25° C.)
20 mM (NH$_4$)$_2$SO$_4$
0.01% (v/v) Tween 20;
2 mM MgCl$_2$
1 μM sense Glia-dp (SEQ ID NO:10)
1 μM antisense Glia-dp (SEQ ID NO:11)

The reaction was incubated for 1 minute at 95° C. and subsequently cooled to 25° C. with a temperature dropping rate of 2° C. per minute.

The hybridized linker fragments were purified using the NucleoSpin® Extract II purification system (MACHEREY-NAGEL GmbH & Co. KG) in compliance with the manufacturer's instructions, and dissolved in 50 μl 5 mM Tris-HCl pH 8,5 each.

The linkers exhibit a 3' ATG overhang at both ends enabling a directional integration in the AdeI-digested pET24e vector.

The 5' phosphorylated and purified linker fragments were subsequently integrated into the AdeI-digested pET24e plasmid by ligation. For ligation, the Rapid DNA Ligation Kit of Fermentas was used according to the manufacturer's instructions. The ligation was then transformed into E. coli BL21 (DE3) (Stratagene).

Positive clones were selected based on kanamycin resistance [50 μg/ml]. The plasmids were isolated from these clones and verified by restriction analysis and DNA sequencing. The DNA sequence encoding the recombinant protein (gliadin analogue fusion peptide GAF(3X)) according to SEQ ID NO:7 is depicted in SEQ ID NO:5, and the sequence of the entire expression plasmid designated pET24e-GAF (3X) is depicted in SEQ ID NO:6. Correct plasmids were selected for the expression, inoculated into 20 ml of antibiotic containing LB medium and incubated at 37° C. until reaching an OD$_{600}$ (d=1 cm) of 0.6. Protein expression is induced by addition of IPTG (end concentration: 1 mM) and subsequently incubated for 3 hours at 37° C. Afterwards the cells were sedimented by centrifugation at 2.200×g for 20 minutes, resuspended in 20 ml PBS, centrifuged again and finally resuspended in 1 ml PBS.

Cell lysis is carried out by addition of one third volume of 4×NuPAGE-LDS sample buffer (Invitrogen), followed by 10 minutes incubation at 70° C. Chromosomal DNA is subsequently fragmented by ultrasound treatment (Branson Sonifier, Level 7, MicroTip).

The cell lysate is transferred onto a nitrocellulose membrane after separation by SDS-PAGE. Thereafter, non-satiated positions of the membrane were blocked by a 15 minute incubation with "universal buffer" (EUROIMMUN) supplemented with 3% (w/v) Milk powder. Then follows a one hour incubation with a mouse monoclonal antibody to His-Tag (Merck Biosciences GmbH) 1:2000 diluted in "universal buffer" supplemented with 3% (w/v) milk powder. The membrane is washed three times for 5 minutes with "universal buffer". In a second incubation step, the antibodies bound to the proteins in the positive case are reacted with a conjugate solution diluted at 1:2000 with "universal buffer" containing alkaline phosphatase-labeled anti-mouse IgG antibodies (Sigma). Thereafter, washing as after the incubation with serum follows. In a third incubation step, the bound antibodies are detected with a NBT/BCIP "substrate solution" (4-nitrobluetetrazolium chloride/chlorobromoindolyl phosphate, EUROIMMUN).

A His-Tag reactive protein whose molecular weight fits the band of the 7.9 kDa size predicted based on the amino acid sequence, can be detected in the Western blot if the (GAF)$_3$ (His)$_6$ construct according to SEQ ID NO:7 is expressed. Cells containing empty plasmid vector do not exhibit this protein.

EXAMPLE 2

Purification of the Trimeric Gliadin Analogue Protein GAF(3X) by Affinity Chromatography The affinity column used is NiNTA spin column (Qiagen) handled according to the manufacturer's instructions.

The cells harvested according to Example 1 are again centrifuged as described, resuspended in 1 ml "TNI-10 buffer" (5 mM Tris-HCl pH 8.0, 300 mM NaCl, 10 mM imidazol) and lysed by a 1 minute ultrasound treatment (Branson Sonifier, Level 7, MicroTip) repeated three times. Insoluble proteins are separated by centrifugation at 21.250×g for ten minutes. 0.5 ml of the supernatant are subsequently loaded on a NiNTA spin column equilibrated with "TNI-10 buffer".

Non-bound or weakly bound proteins are removed from the column by repeated washing with 0.5 ml "TNI-10 buffer". Elution with 0.2 ml "TNI-150-Puffer" (5 mM Tris-HCl pH 8.0, 300 mM NaCl, 150 mM imidazol) follows. The eluted fraction is analyzed by Western blot as in Example 1.

The eluates essentially contain one protein that corresponds to a band of the 7.9 kDa size after staining of the Western blot membrane with Ponceau-S staining solution. In the Western blot, one band of the same size can be seen. This result indicates that after chromatography the expressed protein is essentially free from E. coli components.

EXAMPLE 3

ELISA for the Determination of Antibodies Specific for Celiac Disease and Dermatitis Herpetiformis The ELISA microtiter plates (Maxisorb, Nunc) are coated over night at ambient temperature with antigen diluted in PBS. As especially preferred antigens, we use a recombinant fusion polypeptide combined from an immunologically dominant deamidated nonapeptide of gliadin linked to an artificial octapeptide homologous to gliadin (according to SEQ ID NO:7).

Subsequently, the plates coated with antigen are washed with PBS (0.1% Tween 20) and blocked with PBS 10% fetal calf serum for 2 hours at ambient temperature. Thereafter the microtiter plates are again washed with PBS-0.1% Tween 20. The incubation of the plates is as described in the EUROIMMUNE instruction manuals. The results of the performance assessment of this ELISA are summarized in Table 2.

EXAMPLE 4

Immunotherapeutic Method for the Treatment of Celiac Disease and Dermatitis Herpetiformis Purified antigen of the invention is bound to a solid phase and used as column material for immunoaffinity chromatography. Plasma from a patient with celiac disease or dermatitis herpetiformis is passed through this column in flow mode and infused back into the patient in antibody-depleted form.

The invention claimed is:

1. A polypeptide comprising one or more of a first peptide sequence and one or more of a second peptide sequence wherein the first peptide sequence is SEQ ID NO:2 and the second peptide sequence is SEQ ID NO:3, wherein SEQ ID NO:2 and SEQ ID NO:3 partially overlap, and wherein the binding of the polypeptide to antibodies specific for celiac disease and dermatitis herpetiformis is comparable to the binding of the polypeptide according to SEQ ID NO:7 to the antibodies specific for celiac disease and dermatitis herpetiformis.

2. The polypeptide according to claim 1, wherein the polypeptide comprises one or more polypeptides consisting of at least 10, at least 14, at least 15, or at least 16 successive amino acids of SEQ ID NO:4 or wherein the polypeptide comprises one or more polypeptides according to SEQ ID NO:4.

3. The polypeptide according to claim 1, comprising three polypeptides according to SEQ ID NO:4.

4. The polypeptide according to claim 1, comprising one or several polypeptide sequences according to SEQ ID NO:7.

5. A polymer comprising 2 to 20 polypeptides of claim 1 joined together.

6. The polypeptide according to claim 1, wherein the polypeptide is produced recombinantly or with common biochemical means of polypeptide synthesis.

7. The polypeptide according to claim 1, wherein the polypeptide is bound to a reporter molecule or to a solid phase.

8. A method for the diagnosis of celiac disease or dermatitis herpetiformis, comprising:

contacting a liquid biological sample from a patient with one or several polypeptides under conditions that the binding of antibodies from the biological sample to said polypeptides can take place, wherein the polypeptide comprises one or more of a first peptide sequence and one or more of a second peptide sequence, and wherein (1) the first peptide sequence is SEQ ID NO:2 or a sequence comprising up to 30% of amino acid of SEQ ID NO:2 deleted or substituted by conservative amino acid substitutions, (2) the second peptide sequence is SEQ ID NO:3 or a sequence comprising up to 30% of amino acid sequence of SEQ ID NO:3 deleted or substituted by conservative amino acid substitutions, and (3) the binding of the polypeptide to antibodies specific for celiac disease and dermatitis herpetiformis is comparable to the binding of the polypeptide according to SEQ ID NO:7 to the antibodies specific for celiac disease and dermatitis herpetiformis, and detecting the presence or absence of the antibodies that bind to one of the polypeptides, whereby diagnosing celiac disease or dermatitis herpetiformis.

9. The method according to claim 8, wherein the liquid biological sample from a patient is contacted with at least two different polypeptides.

10. The method according to claim 8, wherein the binding of the antibodies to the fusion polypeptides is detected using an immunofluorescence test, microarray, ELISA, luminescence test, blot, radioimmunoassay, Western blot or dot blot.

11. A test kit for the detection of antibodies, comprising a polypeptide that comprises one or more of a first peptide sequence and one or more of a second peptide sequence, wherein (1) the first peptide sequence is SEQ ID NO:2 or a sequence comprising up to 30% of amino acid of SEQ ID NO:2 deleted or substituted by conservative amino acid substitutions, (2) the second peptide sequence is SEQ ID NO:3 or a sequence comprising up to 30% of amino acid sequence of SEQ ID NO:3 deleted or substituted by conservative amino acid substitutions, and (3) the binding of the polypeptide to antibodies specific for celiac disease and dermatitis herpetiformis is comparable to the binding of the polypeptide according to SEQ ID NO:7 to the antibodies specific for celiac disease and dermatitis herpetiformis.

12. A nucleic acid encoding a polypeptide according to claim 1.

13. The method of claim 8, wherein the first peptide sequence is SEQ ID NO:2 and the second peptide sequence is SEQ ID NO:3, and wherein SEQ ID NO:2 and SEQ ID NO:3 partially overlap.

14. The method of claim 8, wherein the polypeptide comprises one or more polypeptides consisting of at least 10, at least 14, at least 15, or at least 16 successive amino acids of SEQ ID NO:4 or wherein the polypeptide comprises one or more polypeptides according to SEQ ID NO:4.

15. The method according to claim 8, comprising three polypeptides according to SEQ ID NO:4.

16. The method according to claim 8, comprising one or several polypeptide sequences according to SEQ ID NO:7.

* * * * *

UNITED STATES PATENT AND TRADEMARK OFFICE
CERTIFICATE OF CORRECTION

PATENT NO. : 8,124,354 B2  Page 1 of 1
APPLICATION NO. : 12/602321
DATED : February 28, 2012
INVENTOR(S) : Christian Probst et al.

It is certified that error appears in the above-identified patent and that said Letters Patent is hereby corrected as shown below:

On the Title Page, Item (75):
"Christian Probst, Ratzeburg (DE); Wolfgang Schlumberger, Gross Grönau (DE); Winfried Stöcker, Gross Gröcker (DE); Cornelia Dähnrick, Gross Grönau (DE); Lars Komorowski, Ratzeburg (DE); Thomas Mothes, Leipzig (DE)" should read, --Christian Probst, Ratzeburg (DE); Wolfgang Schlumberger, Gross Grönau (DE); Winfried Stöcker, Gross Grönau (DE); Cornelia Dähnrick, Gross Grönau (DE); Lars Komorowski, Ratzeburg (DE); Thomas Mothes, Leipzig (DE)--.

On the Title Page, Item (56):
"Sjöstrom, H. et al., "Identification of a Gliadin T-Cell Epitope in Coeliac Disease: General Importance of Gliadin Deamidation for Intestinal T-Cell Recognition," *Scand. J. Immunol. 48*:111-115, 1998." should read, --Sjöström, H. et al., "Identification of a Gliadin T-Cell Epitope in Coeliac Disease: General Importance of Gliadin Deamidation for Intestinal T-Cell Recognition," *Scand. J. Immunol. 48*:111-115, 1998.--.

Signed and Sealed this
Thirtieth Day of July, 2013

Teresa Stanek Rea
*Acting Director of the United States Patent and Trademark Office*